(12) United States Patent
Li et al.

(10) Patent No.: US 10,041,085 B2
(45) Date of Patent: Aug. 7, 2018

(54) PLANT TYPE RELATED PROTEIN, AND CODING GENE AND APPLICATION THEREOF

(71) Applicant: Cotton Research Institute, Chinese Academy of Agricultural Sciences, Henan (CN)

(72) Inventors: Fuguang Li, Henan (CN); Zuoren Yang, Henan (CN); Chaojun Zhang, Henan (CN); Yufen Wang, Henan (CN); Zhixia Wu, Henan (CN); Chuanliang Liu, Henan (CN); Xueyan Zhang, Henan (CN); Ye Wang, Henan (CN); Fenglian Li, Henan (CN); Qianhua Wang, Henan (CN); Wenqiang Qin, Henan (CN); Depei Kong, Henan (CN)

(73) Assignee: Cotton Research Institute, Chinese Academy of Agricultural Sciences, Henan (CN)

( * ) Notice: Subject to any disclaimer, the term of this patent is extended or adjusted under 35 U.S.C. 154(b) by 0 days.

(21) Appl. No.: 14/782,976

(22) PCT Filed: Apr. 9, 2013

(86) PCT No.: PCT/CN2013/000406
§ 371 (c)(1),
(2) Date: Oct. 7, 2015

(87) PCT Pub. No.: WO2014/166012
PCT Pub. Date: Oct. 16, 2014

(65) Prior Publication Data
US 2017/0130241 A1     May 11, 2017

(51) Int. Cl.
C12N 15/87      (2006.01)
C12N 15/82      (2006.01)
C07K 14/415     (2006.01)

(52) U.S. Cl.
CPC ........ *C12N 15/8261* (2013.01); *C07K 14/415* (2013.01); *C12N 15/8266* (2013.01); *C12N 15/8298* (2013.01)

(58) Field of Classification Search
None
See application file for complete search history.

(56) References Cited

U.S. PATENT DOCUMENTS

| | | | |
|---|---|---|---|
| 6,225,536 B1 | 5/2001 | Kasukabe et al. | |
| 6,509,191 B2 * | 1/2003 | Liu | A01H 5/08 435/320.1 |
| 6,534,313 B1 * | 3/2003 | Neff | C12N 9/0071 435/419 |

FOREIGN PATENT DOCUMENTS

| | | |
|---|---|---|
| CN | 101519662 A | 9/2009 |
| CN | 101624595 B | 2/2012 |
| CN | 102911939 A | 2/2013 |
| CN | 103014061 A | 4/2013 |

OTHER PUBLICATIONS

Kano-Murakami et al (1993, FEBS 334:365-368).*
Bowie et al, Science 247:1306-1310, 1990.*
McConnell et al, Nature 411 (6838):709-713, 2001.*
International Search Report dated Jan. 16, 2014 for PCT/CN2013/000406.

* cited by examiner

*Primary Examiner* — Stuart F Baum
(74) *Attorney, Agent, or Firm* — Knobbe, Martens, Olson & Bear, LLP

(57) ABSTRACT

A plant type related protein, and a coding gene and an application thereof are provided. The protein is: (a) a protein consisting of the amino acid sequence of SEQ ID NO: 1; (b) a SEQ ID NO: 1-derived protein having substitution, deletion, and/or addition of an amino acid residue on the sequence of SEQ ID NO: 1, and related to the plant type and/or inactivation of a plant brassinolide type, or (c) a protein having more than 80% homology to the sequence of SEQ ID NO: 1 and related to a plant type and inactivation of a plant brassinolide type. The protein and its coding gene have very important value in improving crop production, improving the visual enjoyability of a green plant, implementing simple cultivation of a plant and improving the breeding efficiency, and has a broad prospective in genetic improvement of a plant, new variety cultivation and an application.

12 Claims, 5 Drawing Sheets

PLANT TYPE RELATED PROTEIN, AND CODING GENE AND APPLICATION THEREOF

CROSS REFERENCE TO RELATED APPLICATIONS

This application is the U.S. National Phase of International Application No. PCT/CN2013/000406, filed Apr. 9, 2013, designating the U.S. and published in Chinese as WO 2014/166012 A1 on Oct. 16, 2014. Any and all applications for which a foreign or domestic priority claim is identified here or in the Application Data Sheet as filed with the present application are hereby incorporated by reference under 37 CFR 1.57.

INCORPORATION OF THE SEQUENCE LISTING

The material in the accompanying Sequence Listing is hereby incorporated by reference into this application. The accompanying sequence listing text file, named JEEK022.001APC_Substitute SeqListing.txt, was created on Dec. 15, 2016 and is 18 KB. The file can be assessed using Microsoft Word on a computer that uses Windows OS.

TECHNICAL FIELD

The present invention belongs to the field of biotechnology and genetic engineering, and relates to a plant type related protein, and a coding gene and an application thereof, particularly to a cotton plant dwarfing related protein and a coding gene and an application thereof.

BACKGROUND

The term of "plant type" refers to a set of characteristics or an arrangement in space, i.e., features of growth and appearance, of a plant associated with the productivity of a crop variety. An ideal plant type, also called an ideotype, refers to an ideal type of plant formed of characters beneficial to plant photosynthesis, growth and development, and grain production, which allows for a maximal improvement of population optical energy availability, an increased biological yield, and an improved economic coefficient, etc.

One of the important factors of a plant type is plant height, which is not only a dominative factor affecting the plant type of a crop, but also an important agronomical character controlling the production. In order to improve the production of a crop, to facilitate a transition thereof from natural growth to targeted growth, and to lead the growth and development as well as appearance of a plant to promote high production, high quality, low consumption, and high efficiency, recently numerous experimental researches have been made on a production increasing effect of crop dwarfing. The results show that suitable dwarfing of a plant to increase population structure enables an increased production.

Cotton is one of the most important economic crops in China. Cotton is originally a ligneous perennial, and becomes an annual after a long-term naturalization, but retaining the character of indeterminate growth of a ligneous plant. However, big body with luxuriant foliage and spreading branches of the cotton plant often leads to shadowing in field, poor ventilation and light penetration, massive buds and bolls drop, and tendency to lodging, susceptibility of cotton bolls to pathogenic bacteria, formation of rotted and dead bolls, having a severe impact on the production and quality of cotton. Hybrid cotton predominates the south of China, where light, heat, and water are all sufficient during the growth of cotton, to make vegetative growth more vigorous. However, the plant type is more difficult to control, so that a high, big and hallow population tends to occur, resulting in a decreased production. Thus, development of an ideal plant type, and cooperation of the relations between plant development and external environment, vegetative growth and reproductive growth, and individual and population to provide a cotton plant with a reasonable development process adaptive to the characteristics of various ecological regions, is essential to achieve high quality and production of cotton. In the production of cotton, cultivation techniques are mainly used to lower plant height, shorten branches, and reduce leaf size. By way of controlling the growth of vegetative mass, facilitating growth of reproductive organs, to keep ventilation and light penetration in cotton field, to obtain more bolls per acre, and to regulate the economic coefficient of cotton, a higher production is achieved. Currently, among the main crops in China, rice and wheat are produced by use of dwarf varieties, but cotton is forcibly dwarfed by cultivation means, such as regulation with fertilizers, reduction of nutrient supply, inhibition of apical dominance by top pruning, chemical regulation with dimethyl piperidinium chloride (DPC), etc., which require consumption of a large number of labor and fossil energy, increasing costs for cotton production.

SUMMARY

A goal of the present invention is to provide a plant type related protein and a coding gene and an application thereof.

A goal of the present invention is to provide a plant type related protein and a coding gene and an application thereof.

The present invention provides a protein derived from *Gossypium hirsutum*, which is named as protein GhPGD1, and is a protein of following (a) or (b) or (c) or (d) or (e):
(a) a protein consisting of an amino acid sequence presented by SEQ ID NO: 1 in the sequence listing;
(b) a protein derived from SEQ ID NO: 1 with one or more amino acid residues substituted and/or deleted and/or added in the amino acid sequence of SEQ ID NO: 1, and related to a plant type;
(c) a protein derived from SEQ ID NO: 1 having more than 80% homology to the amino acid sequence of SEQ ID NO: 1, and related to a plant type;
(d) a protein derived from SEQ ID NO: 1 with one or more amino acid residue substituted and/or deleted and/or added in the amino acid sequence of SEQ ID NO: 1 and related to inactivation of brassinosteroid of a plant;
(e) a protein derived from SEQ ID NO: 1 having more than 80% homology to the amino acid sequence of SEQ ID NO: 1 and related to inactivation of brassinosteroid of a plant. For facilitating the purification of the protein of (a), a label as shown in Table 1 may be linked to the protein consisting of the amino acid sequence presented by SEQ ID NO: 1 in the sequence listing at an amino or carboxy end.

TABLE 1

Sequence of labels

| Label | Residues | Sequence |
| --- | --- | --- |
| Poly-Arg | 5-6 (usually 5) | RRRRR (SEQ ID NO: 21) |
| Poly-His | 2-10 (usually 6) | HHHHHH (SEQ ID NO: 22) |

TABLE 1-continued

Sequence of labels

| Label | Residues | Sequence |
|---|---|---|
| FLAG | 8 | DYKDDDDK (SEQ ID NO: 23) |
| Strep-tag II | 8 | WSHPQFEK (SEQ ID NO: 24) |
| c-myc | 10 | EQKLISEEDL (SEQ ID NO: 25) |
| HA | 9 | YPYDVPDYA (SEQ ID NO: 26) |

The protein (b) or (c) or (d) or (e) described above may be artificially synthesized, or may be obtained by synthesis of a coding gene and subsequently biological expression thereof. The coding gene of the protein of (b) or (c) or (d) or (e) described above may be obtained by deleting codon(s) of one or more amino acid residue from the DNA sequence of SEQ ID NO: 2 in the sequence listing, and/or by performing missense mutation of one or more base pairs, and/or by linking a coding sequence of the label as shown in Table 1 at 5'-terminus and/or 3'-terminus.

The gene coding protein GhPGD1 as shown also belongs to the scope of the present invention, and designated as a GhPGD1 gene.

The gene may be particularly a DNA molecule of 1) or 2) or 3) or 4) or 5) or 6) or 7) or 8):
1) a DNA molecule having a coding region as presented by nucleotides at positions 133 to 1704 from 5'-terminus of SEQ ID NO: 2 in the sequence listing;
2) a DNA molecule having a coding region as presented by nucleotides at positions 133 to 1707 from 5'-terminus of SEQ ID NO: 2 in the sequence listing;
3) a DNA molecule presented by SEQ ID NO: 2 in the sequence listing;
4) a DNA molecule presented by SEQ ID NO: 3 in the sequence listing;
5) a DNA molecule hybridizing with the DNA sequence defined by 1) or 2) or 3) or 4) in strict conditions and coding a plant type related protein;
6) a DNA molecule having more than 80% homology to the DNA sequence defined by 1) or 2) or 3) or 4) and coding a plant type related protein;
7) a DNA molecule hybridizing with the DNA sequence defined by 1) or 2) or 3) or 4) in strict conditions and coding a protein related to inactivation of brassinosteroid of a plant;
8) a DNA molecule having more than 80% homology to the DNA sequence defined by 1) or 2) or 3) or 4) and coding a protein related to inactivation of brassinosteroid of a plant.

The strict conditions aforementioned may be hybridization in a solution of 6×SSC, 0.5% SDS, at 65° C., and then wash with each of 2×SSC, 0.1% SDS and 1×SSC, 0.1% SDS once.

All of recombinant expression vectors, expression cassettes, transgenic cell lines or recombinant strains containing the GhPGD1 gene are within the scope of the present invention.

The recombinant expression vector containing said gene may be constructed using an existing plant expression vector. The plant expression vector comprises a binary expression vector of Agrobacterium and a vector that may be used for microprojectile bombardment in a plant. The plant expression vector may also comprise a 3'-terminal untranslated region of an exogenous gene, i.e., comprising polyadenylic acid (polyA) signal and any other DNA fragment participating mRNA processing or gene expression. The polyA signal may lead polyA to incorporate into 3'-terminus of mRNA precursor. When the gene is used to construct a recombinant expression vector, any enhanced promoter or constitutive promoter may be added, alone or in combination with other plant promoters, before the transcription starting nucleotide therein; in addition, when the gene of the invention is used to construct a recombinant expression vector, an enhancer, including a translational enhancer or a transcriptional enhancer, may be used, but it must have the reading frame of coding sequence, to ensure a correct translation of the entire sequence. The signal controlling translation and the initiation codon may be from a wide variety of sources, and may be native or synthetic. A translation starting region may be from a transcription starting region or a structural gene. For facilitating the identification and screening of a transgenic plant cell or a plant, the plant expression vector to be used may be processed, for example, adding a gene that may be expressed in a plant and encodes an enzyme or a luminous compound that may develop a change in color, a resistant antibiotic marker, or a chemical resistant marker gene, or the like.

The recombinant expression vector may be particularly a recombinant plasmid obtained by inserting the GhPGD1 gene to vector pCAMBIA2300 at a multiple clone site.

The recombinant expression vector may be particularly a recombinant plasmid obtained by inserting a cassette of the GhPGD1 gene to vector pCAMBIA2300 at a multiple clone site. In the cassette, the expression of the GhPGD1 gene is initiated by a 35S promoter, and terminated by a nos terminator.

The 35S promoter is particularly presented by SEQ ID NO: 4 in the sequence listing. The nos terminator is particularly presented by SEQ ID NO: 5 in the sequence listing.

The recombinant expression vector may be particularly a recombinant plasmid as below: having vector pCAMBIA2300 as backbone, with the 35S promoter inserted between HindIII and XbaI cleavage sites, the GhPGD1 gene inserted between XbaI and SacI cleavage sites, and the nos terminator inserted between SacI and EcoRI cleavage sites.

Each of the GhPGD1 protein, GhPGD1 gene, cassette, recombinant expression vector, transgenic cell line or recombinant strain may be used for improving a plant type. The improvement of a plant type is particularly realized as dwarfing a plant. The plant may be a monocotyledon or a dicotyledon. The dicotyledon may be cotton, and particularly a cotton variety of "CRI 24". The dicotyledon may be Arabidopsis, and particularly Arabidopsis thaliana of ecotype Columbia.

Each of the GhPGD1 protein, GhPGD1 gene, cassette, recombinant expression vector, transgenic cell line or recombinant strain may be used for cultivating a transgenic plant. The transgenic plant may be particularly a plant having a dwarf phenotype. The plant may be a monocotyledon or a dicotyledon. The dicotyledon may be cotton, and particularly a cotton variety of "CRI 24". The dicotyledon may be Arabidopsis, and particularly Arabidopsis thaliana of ecotype Columbia.

The present invention also provides a method for breeding a transgenic plant, by introducing the GhPGD1 gene into a target plant, to obtain a transgenic plant with a plant height less than that of the target plant. An expression vector carrying the gene may be transformed into a plant cell or a tissue by conventional biological methods such as use of a Ti plasmid, a Ri plasmid, a plant virus vector, direct DNA transormation, microinjection, electroconduction, Agrobacterium mediation, etc., and the transformed plant tissue is cultivated into a plant. The GhPGD1 gene may be particularly introduced into the target plant by the recombinant expression vector. The target plant may be a monocotyledon or a dicotyledon. The dicotyledon may be cotton, and particularly a cotton variety of "CRI 24". The dicotyledon may be *Arabidopsis*, and particularly *Arabidopsis thaliana* of ecotype Columbia.

The present invention also provides a method for breeding a transgenic plant, by overexpressing the GhPGD1 gene in a target plant, to obtain a transgenic plant with a plant height less than that of the target plant. The "overexpressing the GhPGD1 gene in a target plant" may be achieved by introducing the gene into the target plant or by promoting the expression of the GhPGD1 gene of the target plant per se (for example, by introducing a promoter or an enhancer to facilitate the expression of the gene). The target plant may be a monocotyledon or a dicotyledon. The dicotyledon may be cotton, and particularly a cotton variety of "CRI 24". The dicotyledon may be *Arabidopsis*, and particularly *Arabidopsis thaliana* of ecotype Columbia.

Brassinosteroids (BRs) is a group of plant specific steroid hormone, broadly found in plant bodies, and regulates many aspects of the growth and development of a plant, including vegetative growth, reproductive growth, sprouting, aging as well as responses to various biological stress and non-biological stress. Brassinosteroids, even at a very low concentration (nmol/L), exhibits extremely high physiological activities, and thus is consisered as a sixth type of plant hormone following auxin, gibberellin, cytomin, abscisic acid and ethylene.

The present invention also provides a method for breeding a transgenic plant, by overexpressing the GhPGD1 gene in a target plant, to obtain brassinosteroids defective transgenic plant. The brassinosteroids defective type is characterized in that the transgenic plant, as compared with the target plant, has at least one of the phenotypes of: ☐ a shortened hypocotyledonary axis; ☐ a reduced plant height; ☐ a shortened petiole and/or sheath; ☐ a delayed flowering; ☐ a prolonged life cycle; ☐ a phenotype having photomorphogenetic responses in dark. The "overexpressing the GhPGD1 gene in a target plant" may be achieved by introducing the GhPGD1 gene into a target plant, or by promoting the expression of the GhPGD1 gene in the target plant per se (for example, by introducing a promoter or an enhancer to facilitate the expression of the gene). The target plant may be a monocotyledon or a dicotyledon. The dicotyledon may be cotton, and particularly a cotton variety of "CRI 24". The dicotyledon may be *Arabidopsis*, and particularly *Arabidopsis thaliana* of ecotype Columbia.

The present invention also provides a method for shaping a plant, by spraying brassinosteroids to a part of a plant (to facilitate merely the sprayed part), so that the plant is grown into a desired shape; wherein the plant may be the transgenic plant obtained by any of the methods described above, a self offspring of the transgenic plant, a hybrid offspring of the transgenic plant, or a backcross offspring of the transgenic plant.

The present invention will be further illustrated by specific examples in conjunction with the Drawings. Following examples are provided for the purpose of better understanding, rather than limitation, of the invention.

DETAILED DESCRIPTION OF CERTAIN EMBODIMENTS OF THE INVENTION

Following examples are intended for better understanding of the invention, but not limitative. All the experimental methods in the following examples are conventional methods, unless otherwise specified. All the experimental materials used in the following examples are commercially available from common biochemical supplies, unless otherwise specified. All the quantitative assays in the following examples are set in triplicate, with the results averaged.

The cotton variety "CRI 24" (expressed as WT): a variety of *Gossypium hirsutum*, which is bred by the Cotton Research Institute, Chinese Academy of Agricultural Sciences, and is commercially available from the Cotton Seed Industry Technology Co., Ltd. or other seed companies.

*Arabidopsis thaliana* of ecotype Columbia (Col-0): commercially available from ABRC (*Arabidopsis* Biological Resource Center).

Plant expression vector pCAMBIA2300 (abbreviated as vector pCAMBIA2300): commercially available from Cambia (http://www.cambia.org/daisy/cambia/585.html). *Agrobacterium* strain LBA4404: commercially available from clontech.

EXAMPLE 1

Acquisition of Cotton GhPGD1 Protein and Coding Gene Thereof

I. Acquisition and Genetic Analysis of a Dwarfed Tightened Mutant of Cotton

Figure 1:
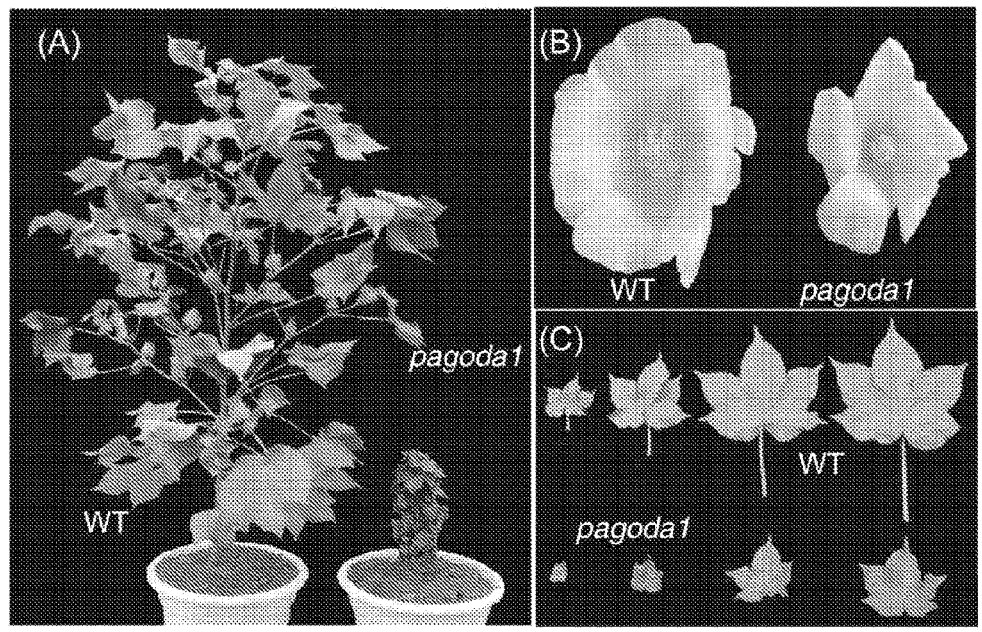
FIG. 1A-C show comparisons of phenotypes between a cotton variety of "CRI 24" and a mutant pagoda1.

Genetic transformation of a cotton variety of "CRI 24" was performed using an activation label to obtain a plant of a dwarfed and tightened mutant, designated as mutant pagoda1 (expressed as pagoda1). A comparison of phenotypes between the cotton variety "CRI 24" (expressed as WT) and mutant pagoda1 may be seen in FIG. 1. As compared with the cotton variety "CRI 24", mutant pagoda1 had an extremely decreased height (FIG. 1A), a reduced floral organ size (FIG. 1B), a shortened petiole (FIG. 1C, a petiole of the top 4th leaf).

The cotton variety "CRI 24" was hybridized with mutant pagoda1, to obtain a $T_0$ hybrid, which was sowed to obtain $T_1$ plants. The phenotype and segregation ratio of the $T_1$ plants were observed. The results showed that the $T_1$ plants exhibited a high-to-short segregation ratio of 1:3 from a seedling stage, and kanamycin application showed that dwarfed and tightened properties were co-separated with a transgenic resistant marker gene NptII, demonstrating that the dwarfed and tightened properties were heritable. In a further genetic assay of $T_2$ plants, the ratio of tall to dwarf of the $T_2$ plants was still shown as 1:3 (see Table 2), consisting with genetic performance controlled by a pair of single dominant genes. Accordingly, the dwarfing mutation was a dominant mutation.

TABLE 2

Separation of $T_2$ plants

| Number of dwarfed plants | Number of normal height plants | Ratio | Chi-Square | DF | Pr > ChiSq |
|---|---|---|---|---|---|
| 85 | 31 | 3:1 | 0.0725 | 1 | 0.7878 |

II. Response of Mutant Pagoda1 to Brassinosteroids

The mutant pagoda1 and the cotton variety"CRI 24" were identified as below, respectively:

Test Group: cultivating cotton plants of the cotyledon stage in a liquid medium containing 500 nM brassinosteroids (Sigma) to the five leaf stage, to measure the length of its hypocotyledonary axis;

Control Group: the same as the Test Group, except that brassinosteroids was replaced with an equal volume of an aqueous solution of 0.2% ethanol.

Figure 2:
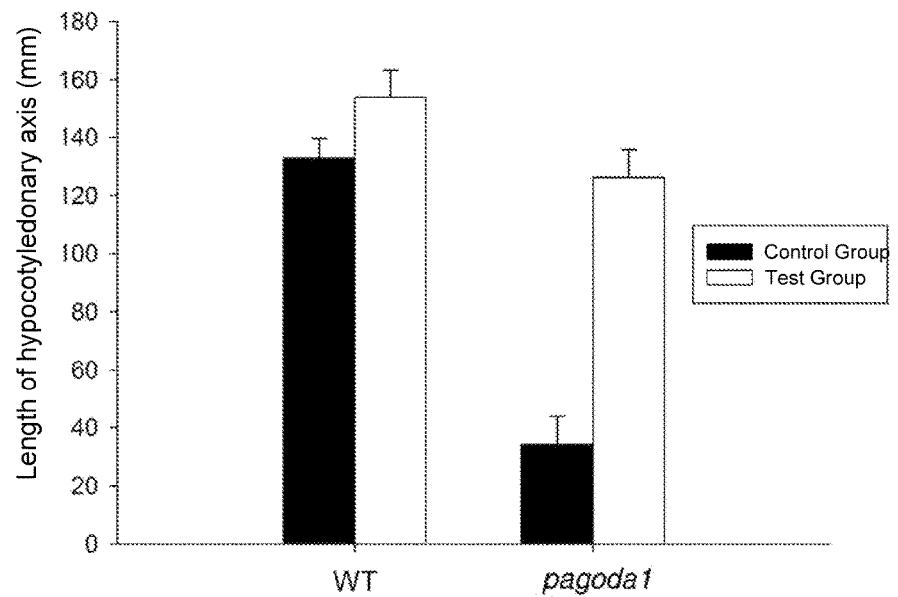
FIG. 2 shows responses of the mutant pagoda1 and the cotton variety "CRI 24" to brassinosteroids.

The length measurements of hypocotyledonary axis of the processed plants from respective groups (an averaged measurement of 20 plants for each group) are shown in FIG. 2. For mutant pagoda1, the hypocotyledonary axis was prolonged by 270% after the treatment with brassinosteroids, comparable to the length of the hypocotyledonary axis of the cotton variety "CRI 24". For the cotton variety "CRI 24", after the treatment with brassinosteroids, the hypocotyledonary axis was prolonged by only 16%. From the results, it is indicated that mutant pagoda1 may be restored by brassinosteroids from a dwarfed phenotype to the phenotype of the cotton variety "CRI 24", that is, mutant pagoda1 is a BRs defective mutant.

III. Photomorphogenetic Response of Mutant Pagoda1

The mutant pagoda1 and the cotton variety "CRI 24" were identified as below:

Illumination Group: cultivating cotton plants in a continuous light condition for 2 weeks, and taking pictures and measuring the length of hypocotyledonary axis;

Dark Group: cultivating cotton plants in a continuous dark condition for 2 weeks, and taking pictures and measuring the length of hypocotyledonary axis.

Figure 3:
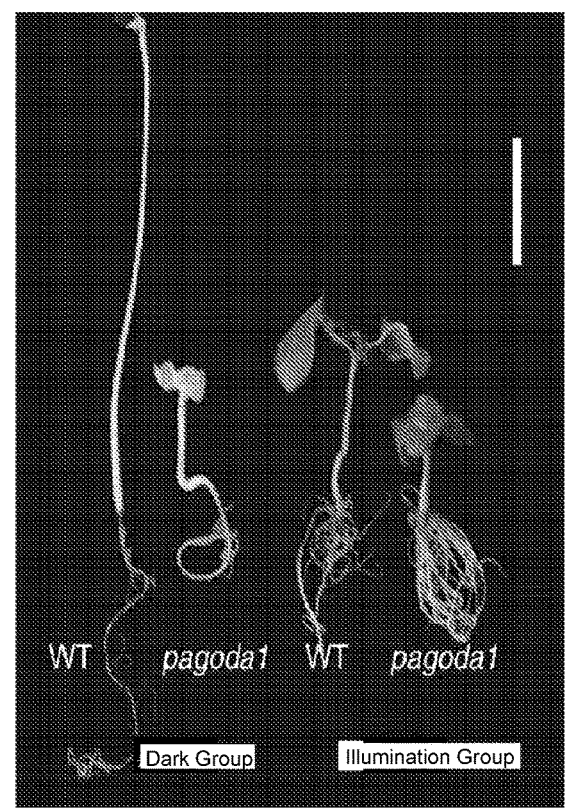
FIG. 3A-B show photomorphogenetic responses of the mutant pagoda1 and the cotton variety "CRI 24".
Figure 3:
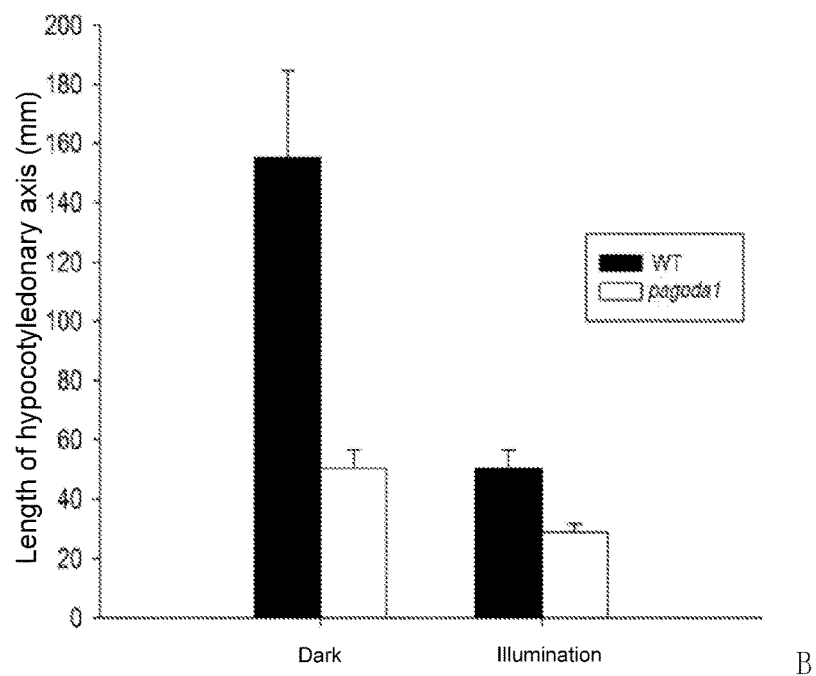

The pictures of the processed plants from respective groups are seen in FIG. 3A, and the length measurements of hypocotyledonary axis of the processed plants from respective groups (an averaged measurement of 20 plants for each group) are shown in FIG. 3B. In dark condition, the cotton variety "CRI 24" had a significantly prolonged hypocotyledonary axis, and exhibited no photomorphogenetic response. In dark condition, as compared with the cotton variety "CRI 24", the mutant pagoda1 had a restricted prolonging of hypocotyledonary axis, and exhibited photomorphogenetic responses such as cotyledon expansion (子叶张开) and hook opening (弯钩打开). These further demonstrate that mutant pagoda1 is a BRs defective mutant.

IV. Shaping of Cotton by Local Application of Brassinosteroids

Figure 4:
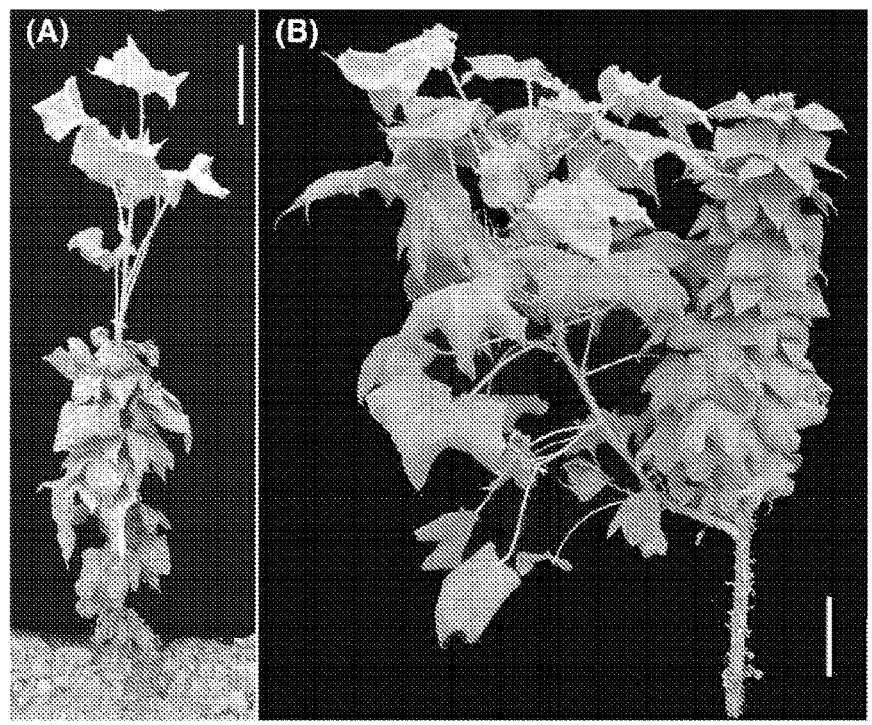
FIG. 4A-B show shaping of cotton by locally applying brassinosteroids.

Since brassinosteroids cannot be delivered for a long distance in a plant, a local application thereof may promote the growth of the applied part, without an impact on the far part. With an application of 500 nM brassinosteroids to the top of a seeding of mutant pagoda1, it was found that brassinosteroids was capable of significantly promoting the growth of the top of the seeding, without affect the rest below the applied part (see FIG. 4A). With an application of 500 nM brassinosteroids to a lateral branch of a seeding of mutant pagoda1, the lateral branch was significantly extended, even to a length more than that of the main stem, while the growth of the main stem was not affected (see FIG. 4B).

V. Acquisition of Cotton GhPGD1 Protein and Coding Gene Thereof

For that the dwarfed and tightened phenotypes were co-separated with T-DNA, a hiTAIL-PCR (Yao-Guang Liu, et al., High-efficiency thermal asymmetric interlaced PCR for amplification of unknown flanking sequences. Yao-Guang Liu and Yuanling Chen. BioTechniques Vol. 43, No. 5: pp 649-656 (November 2007)) method was used for amplifying the flanking sequence at the T-DNA inserting site. TAIL-PCR, also called thermal asymmetric interlaced PCR, can effectively separate an unknown sequence adjacent to a known DNA sequence, which is simple and practicable, effective and sensitive, and capable of obtaining a target fragment in a short time, and thus is a suitable means in molecular-biological studies. In order to improve the success in attempt to obtain a specific, long-fragmental, target product, a substantial modification was made on TAIL-PCR by Professor Yao-Guang Liu, to develop a new method of hiTAIL-PCR, which produced an excellent amplification effect in many species such as rice, *Arabidopsis*, insects, etc.

Three runs of PCR reaction were performed with the genomic DNA of mutant pagoda1 as a template, and nested primers RB-1, RB-2 and RB-3 designed depending on a known T-DNA boundary sequence.

RB-1:
(SEQ ID NO: 6)
5'-CGTGACTGGGAAAACCCTGGCGTT-3';

RB-2:
(SEQ ID NO: 7)
5'-ACGATGGACTCCAGTCCGGCCCAACTTAATCGCCTTGCAGCACATC-3';

RB-3:
(SEQ ID NO: 8)
5'-GAAGAGGCCCGCACCGATCGCCCTT-3'.

The nested primers were paired with random primers and anchor primers to form a 25 µl reaction system, particularly with reference to articles such as Yao-Guang Liu, et al. After three runs of nested PCR, the products were separated with 1% agarose gel, specific bands were recovered with a Promega gel recovery kit, and a T-A cloning was performed according to a pMD18-T kit from TAKARA. The reaction system comprises: 4 µl of DNA fragment (25 ng/ul), 1 µl of T vector, and 5 µl of Solution I, totally 10 µl. After kept in a water bath at 16□ for 1 hour, competent cells of *Escherichia coli* DH5α were transformed, and screened on a LB plate containing Ampicillin for a positive clone, which was picked for sequencing. The results of the sequencing showed that a flanking sequence of 1.5 kb at T-DNA inserting site was obtained.

Primers designed for the T-DNA and flanking sequence were:

```
RB1     5'-CAGATTGTCGTTTCCCGCCTTCAG-3',          (SEQ ID NO: 9)

FL1     5'-TCAGACGAGCAATACTCCACAGCAGG-3'.         (SEQ ID NO: 10)
```

BAC library of pagoda1 existing in our laboratory was screened by pooled PCR. The PCR reaction system was 25 μl, comprising 2.5 μl of 10×Buffer, 2 μl of dNTP Mixture (10 μM), 0.5 μl of Ex Taq (5 μ/μl), 1 μl (125 ng) of BAC library plasmid, 1 μl of upstream primer (10 μM), 1 μl of downstream primer (10 μM), made up with ddH$_2$O to 25 μl. Reaction conditions comprise: initial denaturation at 94° C. for 5 min; at 94° C. for 30 s, at 58° C. for 30 s, at 72° C. for 1 min, for 30 cycles; extension at 72° C. for 5 min. 5 positive clones were screened out, 3 of which were sequenced. The results of the sequencing showed that T-DNA was inserted upstream of the promoter of a gene having a nucleotide sequence presented by SEQ ID NO: 3 in the sequence listing, which was designated as a GhPAGODA1 gene (abbreviated as a GhPGD1 gene).

The GhPGD1 gene had a coding region with a sequence of: nucleotides at positions 1 to 279, 1135 to 1356, 1457 to 1703, 1849 to 2216, and 2356 to 2814 from 5'-terminus of SEQ ID NO: 3 in the sequence listing.

The GhPGD1 gene had a cDNA presented by SEQ ID NO: 2 (1800 bp) in the sequence listing, with an open reading frame of nucleotides at positions 133 to 1707 (1575 bp) from 5'-terminus of SEQ ID NO: 2 in the sequence listing.

The GhPGD1 gene coded the GhPGD1 protein (consisting of 524 amino acid residues) presented by SEQ ID NO: 1 in the sequence listing.

Since the T-DNA region contained a 35S enhancer, mutant pagoda1 with dwarfed and tightened phenotypes might be resulted from an overexpression of the GhPGD1 gene. The leaf total RNA of mutant pagoda1 and cotton variety "CRI 24" were extracted, respectively, and reversely transcribed into a cDNA, which was subjected to Real-time PCR with a pair of primers qpgd1-S and qpgd1-A, to identify the expression level of the GhPGD1 gene. With cotton house-keeping gene, Histone 3, as a reference gene, Real-time PCR was performed using a primer pair of Histone3-S and Histone3-A.

```
qpgd1-S
                                                  (SEQ ID NO: 11)
        5'-CATTGGAAGAAAATCTATGGTGC-3';

qpgd1-A
                                                  (SEQ ID NO: 12)
        5'-ATGATGAGCCCATTTTTCGC-3'.

Histone3-S
                                                  (SEQ ID NO: 13)
        5'-TCAAGACTGATTTGCGTTTCCA-3';

Histone3-A
                                                  (SEQ ID NO: 14)
        5'-GCGCAAAGGTTGGTGTCTTC-3'.
```

Figure 5:
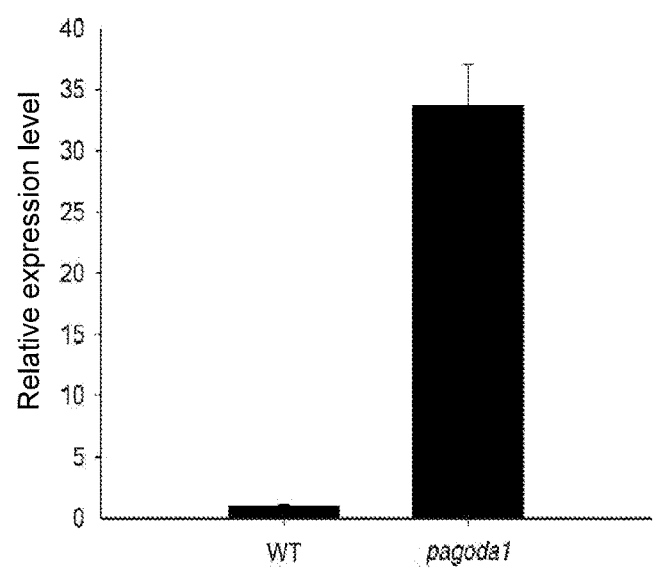
FIG. 5 shows a comparison of relative expression levels of the GhPGD1 gene between the cotton variety "CRI 24" and the mutant pagoda1.

With the relative expression level of the GhPGD1 gene in the cotton variety "CRI 24" being 1, the relative expression level of the GhPGD1 gene in mutant pagoda1 is shown in FIG. 5. The expression level of the GhPGD1 gene in mutant pagoda1 was higher than that of the cotton variety "CRI 24" by 30 folds. Accordingly, it may be confirmed that the dominant dwarfed phenotype of mutant pagoda1 is resulted from an overexpression of the GhPGD1 gene downstream of T-DNA insertion region.

EXAMPLE 2

Acquisition of Transgenic *Arabidopsis* (Overexpression of GhPGD1 Gene)

I. Construction of a Recombinant Expression Vector
1. Total RNA of a leaf from cotton variety "CRI 24" was extracted and reversely transcribed into a cDNA.
2. PCR amplification was performed with the cDNA obtained in step 1 as a template, and a pair of primers pgd1-s and pgd1-a, to obtain products of the PCR amplification.

```
pgd1-s
                                                  (SEQ ID NO: 15)
        5'-GCTCTAGAATGGAGGGTGTTTTACAGTGG-3', pgd1-a
                                                  (SEQ ID NO: 16)
        5'-CGAGCTCTCATGACCCTTGATCTCTTGT-3'.
```

3. The products of the PCR amplification from step 2 were subjected to double-enzyme cleavage with restriction endonucleases XbaI and SacI, to recover cleaved products.
4. A recombinant plasmid pCAMBIA2300-35S-nos was double-cleaved with restriction endonucleases XbaI and SacI, to recover a vector backbone of about 10 kb.

The recombinant plasmid pCAMBIA2300-35S-nos was constructed by a method in which: vector pCAMBIA2300, as a backbone, was inserted with a 35S promoter presented by SEQ ID NO: 4 in the sequence listing between the HindIII and XbaI cleavage sites, and with a nos terminator presented by SEQ ID NO: 5 in the sequence listing between the SacI and EcoRI cleavage sites.
5. The cleaved products from step 3 was linked to the vector backbone from step 4, to obtain a recombinant plasmid pCAMBIA-GhPGD1. As a result of sequencing, the structure of the recombinant plasmidpCAMBIA-GhPGD1 is described as below: having the vector pCAMBIA2300 as backbone, with the 35S promoter presented by SEQ ID NO: 4 in the sequence listing inserted between HindIII and XbaI cleavage sites, with a double stranded DNA molecule presented by nucleotides at positions 133 to 1707 from 5'-terminus of SEQ ID NO: 2 in the sequence listing inserted between XbaI and SacI cleavage sites, and with the nos terminator presented by SEQ ID NO: 5 in the sequence listing inserted between the SacI and EcoRI cleavage sites.

II. Acquisition of Transgenic *Arabidopsis thaliana*
1. A recombinant plasmid pCAMBIA-GhPGD1 was introduced into an *Agrobacterium* strain LBA4404, to obtain a recombinant *Agrobacterium*.
2. The recombinant *Agrobacterium* obtained in step 1 was transformed into *Arabidopsis thaliana* of ecotype Columbia by floral dip, via specific steps as follows:
  (1) seeds of *Arabidopsis thaliana* were sterilized with a solution containing 0.01% (volume ratio) Triton X-100 and 10 g/100 mL NaClO in water for 10 min, and then washed with sterile water in a super-clean bench for 6 times;
  (2) the seeds from step (1) were sowed into a MS medium containing 3.0 g/100 mL sucrose and 0.8 g/100 mL powdered agar, and vernalized for 3-4 days, and subsequently placed in a climate chamber (22□, relative humidity of 70%, light intensity of 150 μmol m$^{-2}$ s$^{-1}$, 12 h illumination/12 h dark), and cultured for 1 week;

(3) seedings from step (2) were transplanted to cultivatable soil (turfy soil and roseite mixed in equal mass; a planter filled with the cultivatable soil was placed in a plastic box containing water prior to transplantation, allowing for water spreading up through a bore at the bottom of the planter, and when the cultivatable soil in the planter was wet through, it was ready for the transplantation), and cultivated as covered by a film for 4 d, and further cultivated with the film removed, for totally 4 weeks from the transplantation (22□, 70% relative humidity, a light intensity of 150 μmol m$^{-2}$ s$^{-1}$, 12 h illumination/12 h dark);

(4) the recombinant *Agrobacterium* obtained in step 1 was suspended in a bacterium suspension (containing sucrose at a concentration of 50 g/L, 200 uL/L silwet-77, and other solutes and concentrations thereof the same as the MS medium), to obtain a bacterium suspension of OD$_{600\ nm}$=0.8;

(5) an entire floral bud of the plant from step (3) was dipped in the bacterium suspension obtained in step (4) for 45 s, and removed and stored in dark for 24 h, and then the plant was normally cultivated for 1 week (22□, 70% relative humidity, a light intensity of 150 μmol m$^{-2}$ s$^{-1}$, 12 h illumination/12 h dark), to harvest T$_1$ seeds;

(6) the T$_1$ seeds were sowed in a MS medium containing 50 mg/L kanamycin, and normally cultivated, to obtain T$_1$ plants.

(7) the T$_1$ plants were subjected to selfing, to obtain T$_2$ seeds.

(8) the T$_2$ seeds were sowed in a MS medium and normally cultivated, to obtain T$_2$ plants.

(9) genomic DNA was extracted from leaves of the T$_1$ and T$_2$, and subjected to PCR identification with a pair of primers pgd1-s and pgd1-a, and a target sequence of about 1.6 kb (for a certain T$_1$ plant, if a corresponding T$_2$ plant thereto was identified as positive by PCR, the T$_2$ plant was considered as a homozygous transgenic plant, and the plant and offspring thereof belong to a single homozygous transgenic plant);

(10) the homozygous transgenic plant (a T$_2$ plant) was subjected to selfing, to obtain T$_3$ seeds.

Totally, 60 homozygous transgenic plants were obtained.

III. Acquisition of *Arabidopsis thaliana* Transfected with an Empty Vector

With a recombinant plasmid pCAMBIA2300-35S-nos instead of recombinant plasmid pCAMBIA-GhPGD1, and the rest the same as above procedure II, *Arabidopsis thaliana* transfected with an empty vector was obtained.

IV. Phenotype Identification

T$_3$ seeds were randomly selected from 5 homozygous transgenic plants (plant 1, plant 2, plant 3, plant 4, and plant 5) (20 seeds of each plant), sowed in soil, and normally cultivated (22□, 70% relative humidity, a light intensity of 150 μmol m$^{-2}$ s$^{-1}$, 12 h illumination/12 h dark), for 30 days counted from the sowing day, and then taken pictures, measured for plant height, and assayed for expression level of GhPGD1 gene. 20 of T$_3$ seeds of *Arabidopsis thaliana* transfected with an empty vector and 20 seeds of *Arabidopsis thaliana* of ecotype Columbia were treated in parallel as controls.

Figure 6:
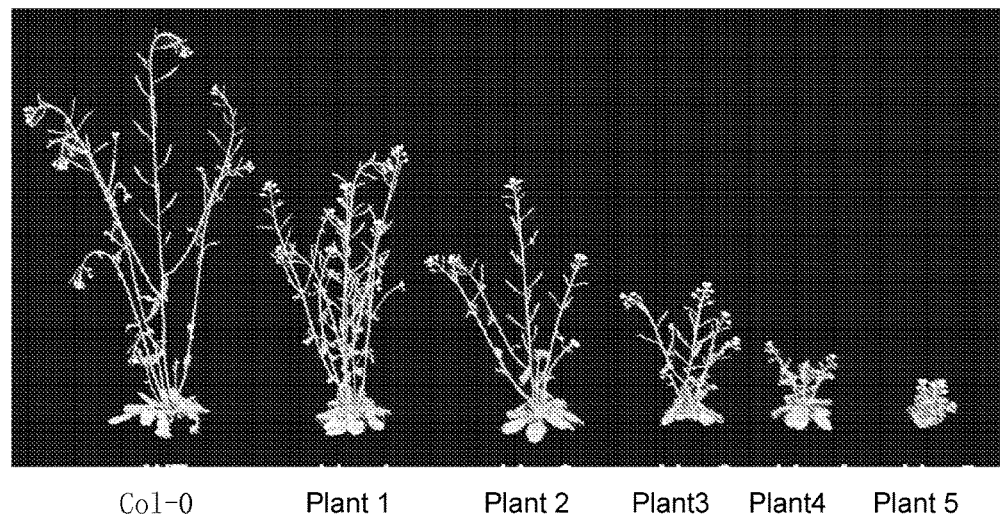
FIG. 6 shows a comparison of phenotypes between *Arabidopsis thaliana* of ecotype Columbia and transgenic *Arabidopsis*.

The pictures of the plant are shown in FIG. 6. Plant 1 had an averaged height of 25.11±1.54 centimeters. Plant 2 had an averaged height of 19.78±2.05 centimeters. Plant 3 had an averaged height of 12.78±1.39 centimeters. Plant 4 had an averaged height of 6.33±1.2 centimeters. Plant 5 had an averaged height of 3.83±0.71 centimeters. *Arabidopsis thaliana* transfected with an empty vector had an averaged height of 31.89±2.15 centimeters. *Arabidopsis thaliana* of ecotype Columbia had an averaged height of 32.17±1.46 centimeters.

Figure 7:
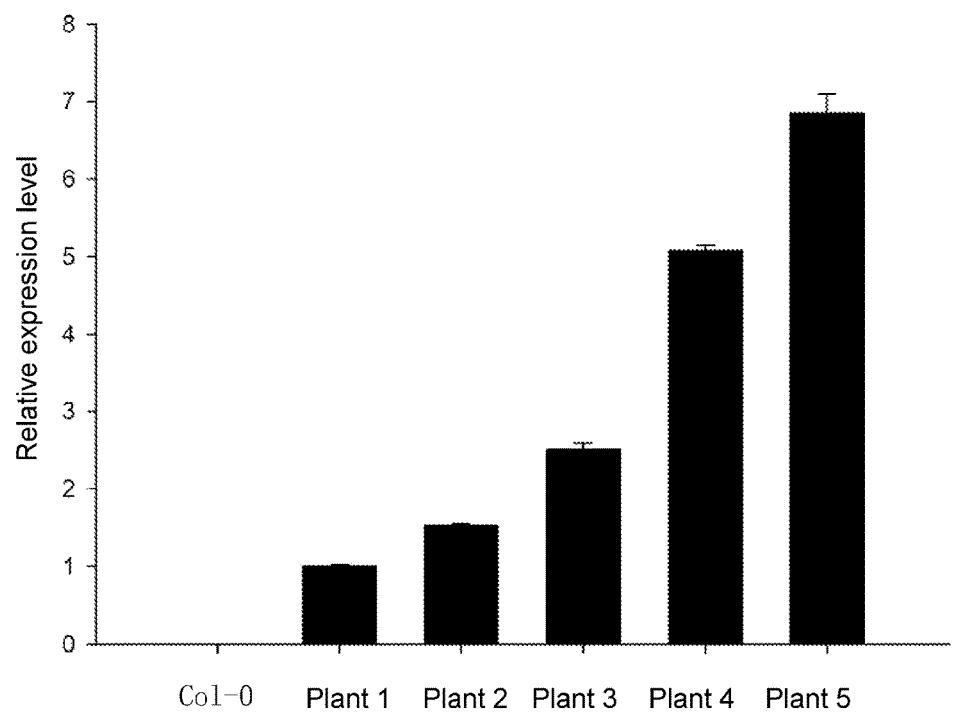
FIG. 7 shows a comparison of relative expression levels of the GhPGD1 gene between *Arabidopsis thaliana* of ecotype Columbia and transgenic *Arabidopsis*.

Total RNA was extracted from a leaf of each of the plants, and reversely transcribed into a cDNA, which was used as a template to perform Real-time PCR with a pair of primers qpgd1-S and qpgd1-A, to identify the expression level of GhPGD1 gene. With actin1 gene as a reference gene, Real-time PCR was performed using a pair of primers actin1-S and actin1-A. The relative expression levels of the GhPGD1 gene in respective plants are shown in FIG. 7. *Arabidopsis thaliana* of ecotype Columbia and the *Arabidopsis thaliana* transfected with an empty vector had no expression of GhPGD1 gene. And the transgenic plants had different expression levels of GhPGD1 gene.

```
qpgd1-S:
                                         (SEQ ID NO: 17)
        5'-CATTGGAAGAAAATCTATGGTGC-3';

qpgd1-A:
                                         (SEQ ID NO: 18)
        5'-ATGATGAGCCCATTTTTCGC-3'.

actin1-S:
                                         (SEQ ID NO: 19)
        5'-ACTCTCCCGCTATGTATGTCGC-3';

actin1-A:
                                         (SEQ ID NO: 20)
        5'-AGAAACCCTCGTAGATTGGCAC-3'.
```

Above results showed that the plant height of *Arabidopsis thaliana* was inversely associated with the expression level of the GhPGD1 gene, that is, a higher expression level of the GhPGD1 gene resulted in a more dwarf phenotype of the plant.

EXAMPLE 3

Aging Delaying Function of GhPGD1 Gene of Cotton

Figure 8:
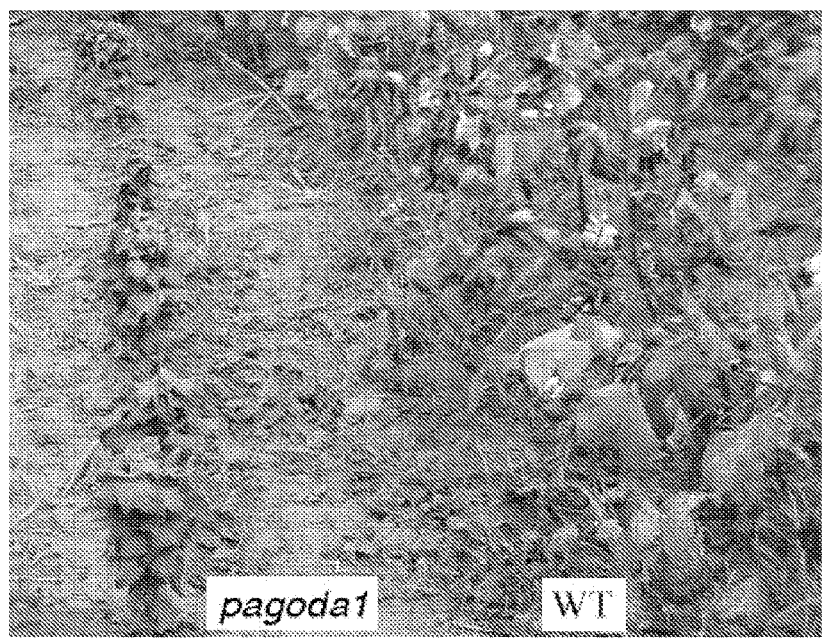
FIG. 8 shows a comparison of growth states between the mutant pagoda1 and the cotton variety "CRI 24" in mid-October at Anyang, Henan, China.

The mutant pagoda1 and the cotton variety "CRI 24" were identified as follows, respectively:

Cotton plants were sowed in field in Anyang at planting time, and subjected to a normal field management. The phenotype thereof was observed and pictured in early October. The pictures are shown in FIG. 8. The cotton variety "CRI 24" had most of leaves yellowing, withered and dropped, and mutant pagoda1 had still dark green leaves, and continuously growable top tissue. The results showed that overexpression of the GhPGD1 gene enables delay of plant aging, prolonging the life cycle of the plant.

EXAMPLE 4

Acquisition of Transgenic Cotton

I. Acquisition of Transgenic Cotton

1. Seeds of a cotton variety of "CRI 24" were stripped off coats, and then dipped with 0.1% mercury bichloride for 5 min for sterilization, washed with sterile water for 3-5 times, and sowed in a sterile seeding cultivation medium (a MS medium+25 g/L of sucrose+6.5 g/L of agar, at pH of 7.0), so as to sprout into sterile seedings.

2. At an aseptic bench, hypocotyledonary axes were excised from the sterile seedings that had grown for 7 days with a scalpel sterilized by an alcohol burner, cut into segments of 0.5-0.8 cm, and dipped with the bacterium suspension of the recombinant *Agrobacterium* from step II. 1 in Example 2 ($OD_{600\ nm}$ value=0.5) for 5 minutes, followed by sucking off of superficial suspension with a filter paper and placement into a callus induction medium (MS medium+30 g/L glucose+0.01 mg/L 2,4-D+0.05 mg/L IAA+0.05 mg/L KT+50 mg/L kanamycin, at pH of 6.5), for cultivation in dark for 48 hours.
3. The resultants were transplanted to a new callus induction medium, and cultivated in an illumination room for 2 months (cultivation conditions: 28☐, 16 h illumination/8 h dark, a light intensity of 150 µmol $m^{-2}$ $s^{-1}$; a subcultivation every 20 days).
4. The resultants were transferred to a regenerate seedling induction medium (MS medium+30 g/L sucrose+0.1 mg/L IAA+0.1 mg/L 6-BA+50 mg/Lkanamycin, at pH of 6.5), and cultivated in the illumination room for 3 months (cultivation conditions: 28☐, 16 h illumination/8 h dark, a light intensity of 150 µmol $m^{-2}$ $s^{-1}$; a subcultivation every 20 days; embryoids started to generate in succession after 1.5 months), to obtain regenerate seedlings.
5. The seedings of the cotton variety "CRI 24" having 4-5 main leaves already were as stock, after the regenerate seedlings were grafted, they were cultivated in a greenhouse (cultivation conditions: 14 h illumination/10 h dark; 28-35☐ in day time, with a light intensity of 150 µmol $m^{-2}$ $s^{-1}$; and 25-28☐ in night time), to obtain $T_1$ seeds.
6. The $T_1$ seeds were sowed and cultivated in a greenhouse (cultivation conditions: 14 h illumination/10 h dark; 28-35☐ in day time, with a light intensity of 150 µmol $m^{-2}$ $s^{-1}$; and 25-28☐ in night time), identified with application of kanamycin, and screened for positive plants, and the $T_1$ plants were subjected to selfing, to obtain $T_2$ seeds.
7. The $T_2$ seeds were sowed and cultivated in a greenhouse (cultivation conditions: 14 h illumination/10 h dark; 28-35☐ in day time, with a light intensity of 150 µmol $m^{-2}$ $s^{-1}$; and 25-28☐ in night time), identified with application of kanamycin, and screened for positive plants.
8. Genomic DNA was extracted from leaves of $T_1$ and $T_2$ plants, and identified by PCR with a pair of primers pgd1-s and pgd1-a, with a target sequence of about 1.6 kb. For a certain $T_1$ plant, if a corresponding $T_2$ plant was identified by PCR as positive, the $T_2$ plant was considered as a homozygous transgenic plant, and the plant and offspring thereof belong to a single homozygous transgenic plant. Totally 16 homozygous transgenic plants were obtained.
9. The homozygous transgenic plants ($T_2$ plants) were selfed, to obtain $T_3$ seeds.

II. Acquisition of Cotton Transfected with an Empty Vector

Cotton transfected with an empty vector was obtained with a recombinant plasmid pCAMBIA2300-35S-nos instead of recombinant plasmid pCAMBIA-GhPGD1, and the rest the same as procedure I.

III. Phenotype Identification $T_3$ seeds were randomly selected from 4 homozygous transgenic plants (plant a, plant b, plant c, plant d) (15 seeds of each plant) and sowed in soil in a sunlight greenhouse. These were observed character, measured, and taken pictures at a full-bloom stage. 20 of $T_3$ seeds of cotton transfected with an empty vector and 20 seeds of the cotton variety "CRI 24" were treated in parallel as controls.

Figure 9:
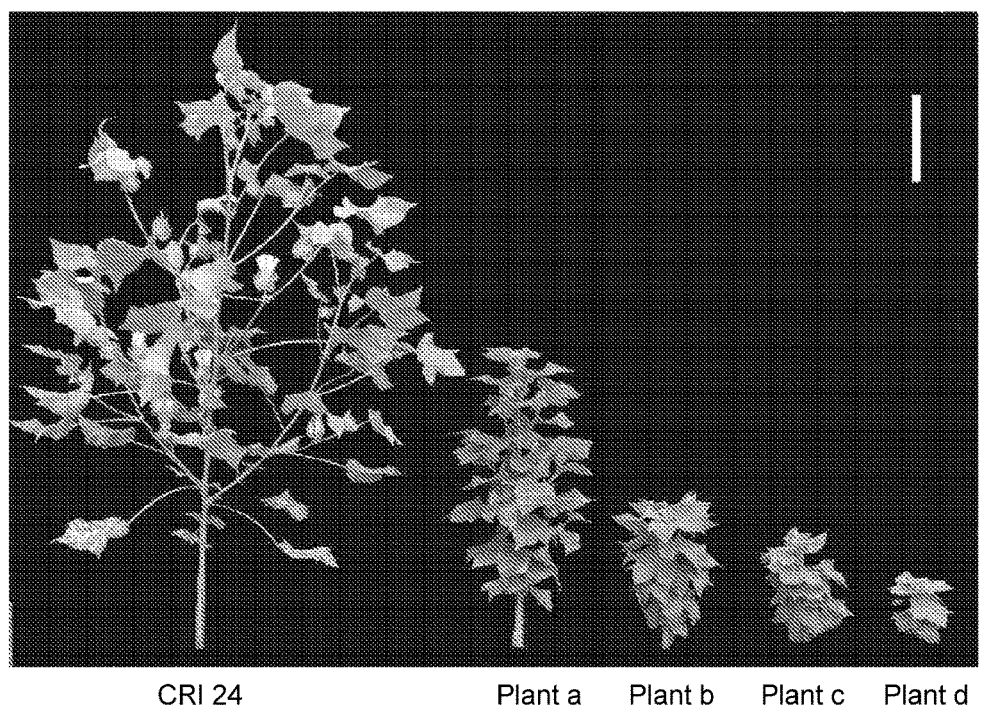
FIG. 9 shows a comparison of phenotypes between the cotton variety "CRI 24" and a transgenic cotton.

The pictures were as in FIG. 9. All of the transgenic plants exhibited shortened branches and internodes, and dwarfed plants. Plant a had an averaged height of 58.77±2.55 centimeters. Plant b had an averaged height of 35.92±2.47 centimeters. Plant c had an averaged height of 29.85±1.99 centimeters. Plant d had an averaged height of 21.77±3.03 centimeters. The cotton transfected with an empty vector had an averaged height of 89.46±3.31 centimeters. CRI 24 had an averaged height of 90.77±3.14 centimeters. These results showed that cotton with an overexpression of GhPGD1 gene had a plant height substantially less than those of the cotton transfected with an empty vector and of the target plant.

INDUSTRIAL APPLICATION

The present invention discloses a protein from cotton related to plant dwarfing and inactivation of brassinosteroids and a coding gene thereof. Overexpression of the gene in a plant allows for a reduction of the amount of endogenous brassinosteroids, which is realized by a shortened hypocotyledonary axis, a dwarfed plant, shortened petioles, shortened internodes, dark green leaves and a prolonged life cycle, as well as photomorphogenesis even in dark. Taking use of this gene, it is possible to improve and shape a plant type, and to delay plant aging. The gene is dominant, which is essential to improve a plant (specifically a crop), shorten breeding time, and increase breeding efficiency. The genetic regulation of cotton plant height with the dwarfing gene and the breeding of a variety having a proper plant height and a desired plant type provided by the present invention are beneficial for making full use of the production potential of light and heat resources and of the space and time advantages of flowering and boll forming of cotton to improve the economic coefficient of cotton, and allow for reducing chemical and artificial regulations, reducing cotton production costs, and improving economic benefits in cotton planting. The protein and coding gene thereof provided by the present invention have very important value in improving the production of a crop (a fruit tree), improving the visual enjoyability of a green plant, implementing a simple cultivation of a plant, and improving a breeding efficiency, and have a broad prospective in genetic improvement of a plant, and new variety cultivation and application.

What is claimed is:

1. A gene comprising a nucleotide sequence encoding the amino acid sequence of SEQ ID NO: 1, wherein said nucleotide sequence is operably linked to a heterologous promoter.

2. The gene according to claim 1, wherein the coding sequence comprises
   (a) the nucleotide sequence as set forth at positions 133 to 1704 of SEQ ID NO: 2;
   (b) the nucleotide sequence as set forth at positions 133 to 1707 of SEQ ID NO: 2;
   (c) the nucleotide sequence of SEQ ID NO: 2; or
   (d) each of the nucleotide sequences as set forth at positions 1 to 279, positions 1135-1356, positions 1457-1703, positions 1849-2216, and positions 2356-2814 of SEQ ID NO: 3.

3. An expression cassette, recombinant expression vector, a transgenic cell line or a recombinant strain comprising the gene of claim 1.

4. A method for producing a transgenic plant, comprising: introducing the gene of claim 1 into a target plant; and selecting a transgenic plant having a decreased plant height relative to the target plant.

5. The method of claim 4, wherein the target plant is a dicotyledon or a monocotyledon.

6. The method of claim 4, wherein the gene is overexpressed in the target plant.

7. The method of claim 6, wherein the overexpression of the gene in the target plant is achieved by operably placing the gene under control of a promoter and/or an enhancer.

8. The method of claim 6, wherein the target plant is a dicotyledon or a monocotyledon.

9. A method for producing a transgenic plant, comprising: overexpressing the gene of claim 1 in a target plant; and selecting a transgenic plant defective in brassinosteroid synthesis.

10. The method of claim 9, wherein the brassinosteroid defective transgenic plant, as compared with the target plant, exhibits one or more phenotypes selected from the group consisting of 1) a shortened hypocotyledonary axis; 2) a reduced plant height; 3) a shortened petiole and/or sheath; 4) a prolonged life cycle; and 5) a photomorphogenetic response in the dark.

11. The method of claim 9, wherein the overexpression of the gene in the target plant is achieved by operably placing the gene under control of a promoter and/or an enhancer.

12. The method of claim 9, wherein the target plant is a dicotyledon or a monocotyledon.

* * * * *

SEQUENCE LISTING

<160> NUMBER OF SEQ ID NOS: 26

<210> SEQ ID NO 1
<211> LENGTH: 524
<212> TYPE: PRT
<213> ORGANISM: Gossypium hirsutum

<400> SEQUENCE: 1

```
Met Glu Gly Val Leu Gln Trp Leu Lys Leu Val Ala Ile Ser Phe Met
1               5                   10                  15

Val Leu Val Leu Val Leu Lys Val Ile Val Leu Leu Trp Trp Arg Pro
            20                  25                  30

Lys Arg Ile Glu Asp His Phe Ser Arg Gln Gly Ile Arg Gly Pro Pro
        35                  40                  45

Tyr His Phe Phe Ile Gly Asn Val Lys Glu Leu Val Gly Met Met Leu
    50                  55                  60

Lys Ala Ser Ser Gln Pro Met Pro Phe Ser His Asn Ile Leu Pro Arg
65                  70                  75                  80

Val Leu Ser Phe Tyr His His Trp Lys Lys Ile Tyr Gly Ala Thr Phe
                85                  90                  95

Leu Val Trp Phe Gly Pro Thr Val Arg Leu Thr Val Ala Asp Pro Asp
            100                 105                 110

Leu Ile Arg Glu Ile Phe Thr Ser Lys Ser Glu Phe Tyr Glu Lys Asn
        115                 120                 125

Glu Ala His Pro Leu Ile Lys Gln Leu Glu Gly Asp Gly Leu Leu Ser
    130                 135                 140

Leu Lys Gly Glu Lys Trp Ala His His Arg Lys Ile Ile Thr Pro Thr
145                 150                 155                 160

Phe His Met Glu Asn Leu Lys Leu Leu Val Pro Leu Val Ala Gln Arg
                165                 170                 175

Val Thr His Met Leu Asp Lys Trp Ser Ala Met Ser Thr Asn Thr Gly
            180                 185                 190

Glu Ile Glu Ile Glu Val Cys Glu Trp Phe Gln Thr Leu Thr Glu Asp
        195                 200                 205

Val Ile Thr Arg Thr Ala Phe Gly Thr Ser Tyr Glu Asp Gly Lys Ala
    210                 215                 220

Ile Phe Arg Leu Gln Ala Gln Gln Met Val Leu Ala Ala Glu Ala Phe
225                 230                 235                 240

Gln Lys Val Phe Ile Pro Gly Tyr Arg Phe Leu Pro Thr Lys Arg Asn
                245                 250                 255

Ile Arg Phe Trp Lys Leu Asp Arg Asp Val Lys Lys Ser Leu Met Lys
            260                 265                 270

Leu Ile Asp Gly Arg Lys Asn Lys Leu Gly Asn Thr Val Gln Glu Lys
        275                 280                 285

Gly Pro Lys Asp Leu Leu Gly Leu Met Met Gln Ala Ser Asn Ser Ser
    290                 295                 300

Pro Asn Val Thr Val His Asp Ile Ile Glu Glu Cys Lys Ser Phe Phe
305                 310                 315                 320

Phe Ala Gly Lys Gln Thr Thr Ser Asn Leu Leu Thr Trp Thr Thr Val
                325                 330                 335

Leu Leu Ala Met His Pro Arg Trp Gln Val Leu Ala Arg Glu Glu Val
            340                 345                 350

Leu Lys Val Cys Gly Ser Arg Asp Ile Pro Ser Lys Asp Val Val
        355                 360                 365

Lys Leu Lys Thr Leu Thr Met Ile Leu Asn Glu Ser Leu Arg Leu Tyr
    370                 375                 380

Pro Pro Thr Ile Ala Thr Ile Arg Arg Ala Lys Ile Asp Ala Lys Leu
385                 390                 395                 400

Gly Gly Tyr Met Ile Pro Arg Asp Thr Glu Leu Leu Ile Pro Ile Leu
                405                 410                 415
```

```
Ala Val His His Asp Gln Thr Ile Trp Gly Asn Asp Ala Asn Glu Phe
            420                 425                 430

Asn Pro Ala Arg Phe Ser Glu Gly Val Ala Arg Ala Ala Lys His Pro
            435                 440                 445

Val Gly Phe Ile Pro Phe Gly Leu Gly Val Arg Thr Cys Ile Gly Gln
            450                 455                 460

Asn Leu Ala Ile Leu Gln Ala Lys Leu Thr Leu Ser Ile Ile Leu Gln
465                 470                 475                 480

Arg Phe Ser Phe Arg Leu Ala Pro Thr Tyr Gln His Ala Pro Thr Val
                485                 490                 495

Leu Met Leu Leu Tyr Pro Gln Tyr Gly Ala Pro Ile Ile Phe Gln Pro
            500                 505                 510

Leu Pro Glu Pro Thr Val Thr Arg Asp Gln Gly Ser
            515                 520

<210> SEQ ID NO 2
<211> LENGTH: 1800
<212> TYPE: DNA
<213> ORGANISM: Gossypium hirsutum

<400> SEQUENCE: 2
gctaaagaag ataagaagca aaaacacaca cacaaaaaaa aggctgctcc acactaagga      60
ggaaaactgt gcgaaaagag agaaaccgaa gctatttgtc tttctttct ttatttcttc     120 ttcttcttcg aaatggaggg tgttttacag tggttgaagc tggttgctat atcattcatg    180
gtgttagttt tggtgttaaa agtgatagtg ttgctttggt ggagaccaaa aaggattgaa    240
gatcatttct caagacaagg gattagagga cctccttacc atttcttcat tggaaatgtt    300
aaggagcttg ttgggatgat gttaaaggct tcttctcaac ctatgccttt tcccacaat    360 atcctcccta gagtcctttc tttctaccat cattggaaga aatctatgg tgcaacattt     420 ctggtttggt ttggcccgac ggttcggctc acggtggccg accctgatct gataagggaa    480
atcttcactt ccaaatccga attctatgaa agaatgaag ctcaccctct tattaaacag     540
ctcgaaggtg atggtctcct tagtctcaaa ggcgaaaat gggctcatca tagaaaaatc    600
ataaccccca ctttccatat ggagaatctc aaattgctag tgccattggt tgcacaaaga   660
gtaacccata tgctcgacaa atggtcggca atgtcgacca acaccggcga gattgaaatc    720
gaagtctgcg aatggtttca gacccttacc gaagatgtca ttactcgtac cgcgtttggg   780
accagttatg aagatggaaa agccattttc cgactacaag cccaacaaat ggtgcttgca   840
gccgaggcat ttcaaaaggt tttcatccct ggttataggt ttttgccgac caagaggaac    900
ataaggtttt ggaaattgga tagggatgtc aaaaaatcgt tgatgaagtt aatcgatgga    960
cggaaaaaca agttggggaa cacagtgcaa gagaaaggac ctaaggattt gctgggatta   1020
atgatgcaag cctcaaattc cagtccaaat gtcacagtcc atgacataat tgaagagtgt   1080
aagagctttt tctttgccgg caaacagacc acatccaatt tgttgacgtg gacgactgtt   1140
cttctagcaa tgcacccacg ctggcaggtg ctcgcacgtg aggaggtgct taaggtgtgt   1200
ggatcacgtg acatacccttc caagatgat gttgtaaagc ttaagacgct cactatgata   1260
ttaaatgaat ctttacgatt atatccacca acaatagcaa caatcagacg agctaaaatt   1320
gatgcaaagc taggggggtta tatgattcct cgtgataccg aacttttgat accgattta    1380 gccgttcatc atgatcaaac catatggggc aacgatgcta atgagttcaa cccggctcgg   1440
ttctccgaag gtgtggcacg tgcagcaaaa catcccgtgg ggttcatccc gtttgggctt   1500
```

| | |
|---|---|
| ggggtccgca cgtgtatcgg gcaaaaccta gccattttac aagccaagtt aacactttcc | 1560 |
| atcatacttc aacgcttctc ctttaggttg gccccaactt atcaacatgc accgactgtt | 1620 |
| ctgatgctac tttacccaca atatggagca ccaatcatct ttcaacctct gccagaaccc | 1680 |
| actgttacaa gagatcaagg gtcatgagtt aatcctatat cgtatatgtg cttatctctt | 1740 |
| gtgtgtgcct gcggcgtatg ctagtaactt gagtgacccc ccccccccca aaaaaaaaaa | 1800 |

<210> SEQ ID NO 3
<211> LENGTH: 2814
<212> TYPE: DNA
<213> ORGANISM: Gossypium hirsutum

<400> SEQUENCE: 3

| | |
|---|---|
| atggagggtg ttttacagtg gttgaagctg gttgctatat cattcatggt gttagttttg | 60 |
| gtgttaaaag tgatagtgtt gctttggtgg agaccaaaaa ggattgaaga tcatttctca | 120 |
| agacaaggga ttagaggacc tccttaccat ttcttcattg gaaatgttaa ggagcttgtt | 180 |
| gggatgatgt taaaggcttc ttctcaacct atgccttttt cccacaatat cctccctaga | 240 |
| gtcctttctt tctaccatca ttggaagaaa atctatggta tgttttcatt aatcttttgt | 300 |
| gggcctgtgt ctaaaaatgt gttaatgtgg gttcttttca gttcattgtt aaagcaaaga | 360 |
| aaagagttga aggaatggat cttcttgttc ttcattttg taaaaaaaaa attatttctg | 420 |
| atcaatgaaa attttatgtc ttgtaaaaaa aaaaaaagca tttgttttg gttatttgag | 480 |
| ttcgggttaa cttacagcc ttttcagtgc tttgatgctt gatgttgaag ttcaggaatt | 540 |
| tttggacggt tccacttctg ttttcttctc tttcttttt atttcttccc ttctttttctt | 600 |
| gcactctctt cttaatgaac aaaaataaac cttgattttc ataatcccat ttctctctct | 660 |
| ctcacacact atatatatac acctatgtgt gtatatattt ctatccttt caacatactt | 720 |
| tactatcttt tctctgtttt tttatatgtg tcatcttcct tttgtttta taggagggttt | 780 |
| gagtttctga taatgaagtt atgttatgtt tgctagtacc actgttgctt tgagttgtct | 840 |
| tcttccctac tttctttcgg cttttaattt aattttctct gcgctccctc gttttctttt | 900 |
| tataaatata tatgttttgc tacagtactc tctatatata catatccatc atcatttcgt | 960 |
| tttgaatttt aatttaatgg cttgtcattt cttttcctgc tccttttcct cttttgcaaa | 1020 |
| cttgatactt accacttgag gttccctgcc cctccctcct tggtgtaaat ccctttttt | 1080 |
| ttttttttc atttttcat ttataacaat aaatattgtt taatatgtgc aggtgcaaca | 1140 |
| tttctggttt ggtttggccc gacggttcgg ctcacggtgg ccgaccctga tctgataagg | 1200 |
| gaaatcttca cttccaaatc cgaattctat gaaaagaatg aagctcaccc tcttattaaa | 1260 |
| cagctcgaag gtgatggtct ccttagtctc aaaggcgaaa atgggctca tcatagaaaa | 1320 |
| atcataaccc ccactttcca tatggagaat ctcaaagtaa tttatccctc atttattact | 1380 |
| tcattcattt ctcatattaa tgattaaccc caccaatcaa gttattaat actccattct | 1440 |
| cttttttat ttgcagttgc tagtgccatt ggttgcacaa agagtaaccc atatgctcga | 1500 |
| caaatggtcg gcaatgtcga ccaacaccgg cgagattgaa atcgaagtct gcgaatggtt | 1560 |
| tcagaccctt accgaagatg tcattactcg taccgcgttt gggaccagtt atgaagatgg | 1620 |
| aaaagccatt ttccgactac aagcccaaca atggtgcctt gcagccgagg catttcaaaa | 1680 |
| ggttttcatc cctggttata ggtaaaaatt atttaaaatt cctgtatatc atcaatcatt | 1740 |
| acaaccgtca tccttggtcc tagattttca cgtatcgaag gtttcagttc cttgtcgtaa | 1800 |

```
tactatacga aatgtctaaa tttgggatat atatttggat tttcaggtttt ttgccgacca    1860 agaggaacat aaggttttgg aaattggata gggatgtcaa aaatcgttg atgaagttaa     1920 tcgatggacg gaaaaacaag ttggggaaca cagtgcaaga gaaaggacct aaggatttgc    1980
tgggattaat gatgcaagcc tcaaattcca gtccaaatgt cacagtccat gacataattg    2040
aagagtgtaa gagcttttc tttgccggca aacagaccac atccaatttg ttgacgtgga     2100
cgactgttct tctagcaatg cacccacgct ggcaggtgct cgcacgtgag gaggtgctta    2160
aggtgtgtgg atcacgtgac ataccttcca agatgatgt tgtaaagctt aagacggtaa     2220
aatatcccta acacccttc cttttgcatt aaagataaaa ctcatatgtt ttgtgtcttt     2280
ttgggtataa attgtgaata ggtaaatgta gttgagaaaa cattctaatt ttgaaattac    2340
atgttgtgtg tgcagctcac tatgatatta aatgaatctt tacgattata tccaccaaca    2400
atagcaacaa tcagacgagc taaaattgat gcaaagctag ggggttatat gattcctcgt    2460
gataccgaac ttttgatacc gattttagcc gttcatcatg atcaaaccat atggggcaac    2520
gatgctaatg agttcaaccc ggctcggttc tccgaaggtg tggcacgtgc agcaaaacat    2580
cccgtggggt tcatcccgtt tgggcttggg gtccgcacgt gtatcgggca aaacctagcc    2640 atttttacaag ccaagttaac acttcccatc atacttcaac gcttctcctt taggttggcc    2700
ccaacttatc aacatgcacc gactgttctg atgctacttt acccacaata tggagcacca    2760
atcatctttc aacctctgcc agaacccact gttacaagag atcaagggtc atga          2814

<210> SEQ ID NO 4
<211> LENGTH: 835
<212> TYPE: DNA
<213> ORGANISM: Artificial sequence
<220> FEATURE:
<223> OTHER INFORMATION: Synthetic sequence

<400> SEQUENCE: 4
agattagcct tttcaatttc agaaagaatg ctaacccaca gatggttaga gaggcttacg      60
cagcaggtct catcaagacg atctacccga gcaataatct ccaggaaatc aaatacattc    120
ccaagaaggt taaagatgca gtcaaaagat tcaggactaa ctgcatcaag aacacagaga    180
aagatatatt tctcaagatc agaagtacta ttccagtatg gacgattcaa ggcttgcttc    240
acaaaccaag gcaagtaata gagattggag tctctaaaaa ggtagttccc actgaatcaa    300
aggccatgga gtcaaagatt caaatagagg acctaacaga actcgccgta aagactggcg    360
aacagttcat acagagtctc ttacgactca atgacaagaa gaaaatcttc gtcaacatgg    420
tggagcacga cacacttgtc tactccaaaa atatcaaaga tacagtctca gaagaccaaa    480
gggcaattga acttttcaa caaagggtaa tatccggaaa cctcctcgga ttccattgcc    540
cagctatctg tcactttatt gtgaagatag tggaaaagga aggtggctcc tacaaatgcc    600
atcattgcga taaggaaag gccatcgttg aagatgcctc tgccgacagt ggtcccaaag    660
atggaccccc acccacgagg agcatcgtgg aaaagaaga cgttccaacc acgtcttcaa     720
agcaagtgga ttgatgtgat atctccactg acgtaaggga tgacgcacaa tcccactatc    780
cttcgcaaga cccttcctct atataaggaa gttcatttca tttggagaga acacg          835

<210> SEQ ID NO 5
<211> LENGTH: 255
<212> TYPE: DNA
<213> ORGANISM: Artificial sequence
<220> FEATURE:
<223> OTHER INFORMATION: Synthetic sequence
```

<400> SEQUENCE: 5

```
gatcgttcaa acatttggca ataaagtttc ttaagattga atcctgttgc cggtcttgcg    60
atgattatca tataatttct gttgaattac gttaagcatg taataattaa catgtaatgc   120
atgacgttat ttatgagatg ggtttttatg attagagtcc cgcaattata catttaatac   180
gcgatagaaa acaaaatata gcgcgcaaac taggataaat tatcgcgcgc ggtgtcatct   240
atgttactag atcgg                                                    255
```

<210> SEQ ID NO 6
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer RB-1

<400> SEQUENCE: 6

```
cgtgactggg aaaccctgg cgtt                                            24
```

<210> SEQ ID NO 7
<211> LENGTH: 46
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer RB-2

<400> SEQUENCE: 7

```
acgatggact ccagtccggc ccaacttaat cgccttgcag cacatc                   46
```

<210> SEQ ID NO 8
<211> LENGTH: 25
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer RB-3

<400> SEQUENCE: 8

```
gaagaggccc gcaccgatcg ccctt                                          25
```

<210> SEQ ID NO 9
<211> LENGTH: 24
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer RB1

<400> SEQUENCE: 9

```
cagattgtcg tttcccgcct tcag                                           24
```

<210> SEQ ID NO 10
<211> LENGTH: 26
<212> TYPE: DNA
<213> ORGANISM: Artificial Sequence
<220> FEATURE:

<223> OTHER INFORMATION: Synthetic Polynucleotide
<220> FEATURE:
<221> NAME/KEY: misc_feature
<223> OTHER INFORMATION: primer FL1

<400> SEQUENCE: 10
tcagacgagc aatactccac agcagg 26

<210> SEQ ID NO 11
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer qpgd1-S

<400> SEQUENCE: 11
cattggaaga aaatctatgg tgc 23

<210> SEQ ID NO 12
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer qpgd1-A

<400> SEQUENCE: 12
atgatgagcc cattttttcgc 20

<210> SEQ ID NO 13
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer Histone3-S

<400> SEQUENCE: 13
tcaagactga tttgcgtttc ca 22

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer Histone3-A

<400> SEQUENCE: 14
gcgcaaaggt tggtgtcttc 20

<210> SEQ ID NO 15
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer pgd1-s

```
<400> SEQUENCE: 15
gctctagaat ggagggtgtt ttacagtgg                                    29

<210> SEQ ID NO 16
<211> LENGTH: 28
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer pgd1-a

<400> SEQUENCE: 16
cgagctctca tgacccttga tctcttgt                                     28

<210> SEQ ID NO 17
<211> LENGTH: 23
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer

<400> SEQUENCE: 17
cattggaaga aaatctatgg tgc                                          23

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer

<400> SEQUENCE: 18
atgatgagcc cattttcgc                                               20

<210> SEQ ID NO 19
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer

<400> SEQUENCE: 19
actctcccgc tatgtatgtc gc                                           22

<210> SEQ ID NO 20
<211> LENGTH: 22
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: primer

<400> SEQUENCE: 20
agaaaccctc gtagattggc ac                                           22
```

```
<210> SEQ ID NO 21
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: Poly-Arg

<400> SEQUENCE: 21

Arg Arg Arg Arg Arg
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: Poly-His

<400> SEQUENCE: 22

His His His His His His
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: FLAG

<400> SEQUENCE: 23

Asp Tyr Lys Asp Asp Asp Asp Lys
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: Strep-tag II

<400> SEQUENCE: 24

Trp Ser His Pro Gln Phe Glu Lys
1               5

<210> SEQ ID NO 25
<211> LENGTH: 10
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: c-myc

<400> SEQUENCE: 25

Glu Gln Lys Leu Ile Ser Glu Glu Asp Leu
```

-continued

```
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<223> OTHER INFORMATION: HA

<400> SEQUENCE: 26

Tyr Pro Tyr Asp Val Pro Asp Tyr Ala
1               5
```